US010016503B2

(12) United States Patent
Klaasen et al.

(10) Patent No.: US 10,016,503 B2
(45) Date of Patent: *Jul. 10, 2018

(54) **IMMUNOGENIC COMPOSITION OF KILLED *LEPTOSPIRA* BACTERIA**

(71) Applicant: Intervet Inc., Madison, NJ (US)

(72) Inventors: Henricus Leo Bernardus Maria Klaasen, Wijchen (NL); Eric Onno Rijke, Boxmeer (NL)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,465

(22) Filed: Oct. 7, 2016

(65) Prior Publication Data

US 2017/0021024 A1      Jan. 26, 2017

Related U.S. Application Data

(62) Division of application No. 14/420,946, filed as application No. PCT/EP2013/067133 on Aug. 16, 2013, now Pat. No. 9,480,734.

(30) Foreign Application Priority Data

Aug. 17, 2012 (EP) .................................. 12180793

(51) Int. Cl.
| | |
|---|---|
| A61K 47/18 | (2017.01) |
| A61K 9/08 | (2006.01) |
| A61K 47/02 | (2006.01) |
| A61K 39/02 | (2006.01) |
| A61K 39/00 | (2006.01) |

(52) U.S. Cl.
CPC .............. *A61K 47/183* (2013.01); *A61K 9/08* (2013.01); *A61K 39/0225* (2013.01); *A61K 47/02* (2013.01); *A61K 2039/521* (2013.01)

(58) Field of Classification Search
CPC .......... A61K 2039/552; A61K 2039/70; A61K 2039/521; A61K 39/0225; A61K 2039/545; A61K 2039/55566; A61K 38/00; A61K 39/04; A61K 39/12; A61K 49/0004; A61K 39/105; A61K 2039/54; A61K 39/00; A61K 39/0208

See application file for complete search history.

(56) References Cited

U.S. PATENT DOCUMENTS 3,917,819 A    11/1975  Yoshioka et al.
9,480,734 B2 * 11/2016  Klaasen ............. A61K 39/0225

FOREIGN PATENT DOCUMENTS

| FR | 3364 M | 5/1965 |
|---|---|---|
| WO | 9318747 A1 | 9/1993 |
| WO | 2004026336 A1 | 4/2004 |
| WO | 2006038115 A1 | 4/2006 |
| WO | WO2006078294 A3 | 5/2007 |
| WO | 2009085912 A1 | 7/2009 |

OTHER PUBLICATIONS

De Queiroz-Leite et al 1996, Rev Latinoam Microbiol. 1996;38:39-43.*
NobivaC L4 , Jul. 2012.*
Wu et al 1989 Wei Sheng Wu Xue Bao.29(5):3903.*
Brandau, et al., Thermal Stability of Vaccines, Journal of Pharmaceutical Sciences, 2003, 218-231, 92-2.
English Translation of FR3364M issued Jun. 8, 1965, Behringwerke Aktiengesellschaft, using internet translation of service on Apr. 14, 2017, 3 pages.
De Queiroz-Leite, et al, Experimental Immunization of Hamsters with an EDTA Extract of Leptospira interrogans, Serovar icterohaemorrhagiae, Rev Latinoam Microbiol, 1996, pp. 39-43, 38.
European Search Report for 12180793.7, dated Nov. 30, 2012, 8 pages.
International Search Report for PCT/EP2013/067133, dated Oct. 7, 2013, 10 pages.
Klaasen, H.L.B.M. et al., Duration of immunity in dogs vaccinated against leptosplrosis with a bivalent inactivated vaccine, Veterinary Microbiology, 2003, pp. 121-132, 95.
Kristensen, D et al., Vaccine stabilization: Research, commercialization, and potential impact, Vaccine, 2011, pp. 7122-7124, 29.
Laurichesse, H. et al., Safety and immunogenicity of subcutaneous or intramuscular administration of a monovalent inactivated vaccine against Leptospira interrogans serogroup Icterohaemorrhagiae in healthy volunteers, Clinical Microbiology and Infection, Apr. 2007, pp. 395-403, vol. 13, No. 1.
Naiman B.M. et al., Protective killed Leptospira borgpetersenii vaccine induces potent Th1 immunity compromising responses by CD4 and γ6 T Lymphocytes, Infection and Immunity, 2001, pp. 7550-7558, vol. 69, No. 12.
Novibac L4—Advertising Brochure. MSD Animal Health. 2012.
Srivastava, SK, Prospects of developing leptospiral vaccines for animals, Indian Journal of Medical Microbiology, 2006, pp. 331-336, vol. 24, No. 4.
Wang, Instability, stabilization, and formulation of liquid protein pharmaceuticals, 1999, pp. 129-188, vol. 185, Int J Pharm.
Wu et al., Studies on Endotoxin of Leptospira v. The Effect of EDTA-Na on the Release of the LPS of Leptospira Interrogans Serovar LAI, Acta Microbiologica Sinica, 1989, pp. 393-395, 29(5).

* cited by examiner

*Primary Examiner* — Padmavathi Baskar

(57) ABSTRACT

The present invention pertains to a composition containing an immunogenic cell preparation of killed *Leptospira* bacteria in an ethylenediaminetetraacetic acid solution. The invention also pertains to a vaccine to protect an animal against an infection with *leptospira* bacteria, wherein the vaccine comprises this composition. Also, the invention pertains to the use of ethylenediaminetetraacetic acid to stabilize an immunogenic preparation of killed *Leptospira* bacteria in a liquid carrier, by dissolving the ethylenediaminetetraacetic acid in the carrier.

11 Claims, No Drawings

IMMUNOGENIC COMPOSITION OF KILLED *LEPTOSPIRA* BACTERIA

CROSS-REFERENCE TO RELATED APPLICATIONS

This application is a divisional application of co-pending U.S. patent application Ser. No. 14/420,946, filed on Feb. 11, 2015, which is a national stage entry under 35 U.S.C. § 371 of PCT/EP2013/067133, filed on Aug. 16, 2013, which claims priority to EP Application No. EP12180793.7, filed on Aug. 17, 2012. The contents of U.S. patent application Ser. No. 14/420,946 and PCT/EP2013/067133 are hereby incorporated by reference in their entireties.

FIELD OF THE INVENTION

The present invention pertains to a composition containing an immunogenic cell preparation of killed *Leptospira* bacteria, a vaccine to protect an animal against an infection with *leptospira* bacteria, and the use of an acid acid to stabilise an immunogenic preparation of killed *Leptospira* bacteria.

BACKGROUND ART

Leptospirosis is a world-wide zoonosis caused by infection with any of the many pathogenic serovars of *Leptospira*. The genus of the organisms is tremendously variable and contains in excess of 250 serovars. The prevalence of individual pathogenic serovars varies in different locales, probably influenced by such factors as climate, indigenous fauna and agricultural practices. Leptospirosis affects virtually all mammalian species. Human leptospirosis also is important and occurs endemically in the tropics and as epidemics in temperate climates. However, unlike other species, humans are not important in the maintenance of the disease in nature, and human-to-human transmission is rare.

Human vaccination against leptospirosis is a goal of the research community but progress has been extremely slow. Given the fact that canine leptospirosis is an important disease and that dogs are a source of leptospirosis, many vaccines are available against the canine disease. Commercial canine leptospirosis vaccines traditionally contain inactivated antigens of serogroups Canicola and Icterohaemorrhagiae (Ictero), and have been available for more than fifty years. Recent recommendations for Europe are to continue inclusion in the vaccine of antigen of serogroups Canicola and Ictero, plus the inclusion of antigen of serogroups *Grippotyphosa* (Grippo) and Australis. Whereas in the USA currently four canine vaccines with antigens of four serogroups (Canicola, ictero, Grippo and Pomona) are available, in Europe a number of traditional bivalent vaccines (Canicola, Ictero) and only one trivalent vaccine (Canicola, Ictero and Grippo) are currently available.

Most commercially available leptospirosis vaccines, if not all, comprise an immunogenic cell preparation of killed *Leptospira* bacteria, such as for example formaline killed whole cells. These vaccines are known to be very stable at a storage temperature well below room temperature, typically between 2° C. and 8° C. However, especially given the fact that leptospirosis is endemic in the tropics, it would be an important advantage of having vaccine stability at a temperature above room temperature, since this would allow storage under ambient conditions, not needing any cooling equipment. In the past, it has been tested whether denaturating any proteins that are present in such killed whole cell vaccines (for example by applying a heat shock treatment that does not affect the leptospira antigens), since such proteins might be responsible for the de-stability of the leptospira antigens, might lead to a significant improvement of the stability. The result however was negative.

OBJECT OF THE INVENTION

There is a need for significantly improving the stability of compositions comprising an immunogenic cell preparation of killed *Leptospira* bacteria, in particular to arrive at a composition which still is effective in evoking an immune response, even after at least a three months storage at a temperature above room temperature. In particular, there is a need for a leptospirosis vaccine, which remains effective, at least in aiding in preventing an infection with *Leptospira* bacteria, even after a three month storage of the vaccine at 37° C., in particular after a nine month storage at this temperature.

SUMMARY OF THE INVENTION

In order to meet the object of the invention, a composition according to the preamble has been devised, wherein the immunogenic cell preparation of killed *Leptospira* bacteria is present in an ethylenediaminetetraacetic acid solution (wherein the term "acid" includes the conjugated base of the acid). It has been shown that be having the antigens present in this solution, the stability of the antigens is markedly improved. A vaccine according to the present invention stored for at least three months at 37° C. retaining an antigenic mass level sufficient to provide almost full protection against an infection with *Leptospira* bacteria.

Definitions

A vaccine in the sense of this invention is a constitution suitable for application to an animal (including humans), comprising one or more antigens, typically combined with a pharmaceutically acceptable carrier such as a liquid containing water, optionally comprising immune stimulating agents (adjuvants), salts, buffers, preservatives, viscosity modifiers etc., which upon administration to the animal induces an immune response for treating a disease or disorder, i.e. aiding in preventing, ameliorating or curing the disease or disorder.

A carrier is a means for carrying the antigens in order to be able and present them in a practical form. Typical carriers are water or other hydrophilic liquids, but solid particles are also commonly used (for example for antigens administered via a dry powder nebuliser).

A cell preparation of killed bacteria is a preparation in essence containing killed bacterial cells, optionally further treated (which may include at least partly lysing the cells) for example to arrive at more stable or more immunogenic preparation. A cell preparation is opposed to a preparation that comprises an extract of bacterial cells such as extracted surface proteins and/or polysaccharides.

Embodiments of the Invention

In an embodiment the solution comprises 5 to 50 mmols of ethylenediaminetetraacetic acid per liter. Preferably the solution comprises 20 mmols of ethylenediaminetetraacetic acid per liter. This range has proven to lead to an effective increase in stability wile at the same time expected to be safe upon administration.

In another embodiment the solution contains dibasic sodium phosphate.

In yet another embodiment the *Leptospira* bacteria are chosen from *Leptospira interrogans* serogroup Canicola serovar Portland-Vere, *Leptosira interrogans* serogroup Australis serovar Bratislava, *Leptospira interrogans* serogroup Icterohaemorrhagiae serovar Copenhageni and *Leptospira kirschneri* serogroup *Grippotyphosa* serovar Dadas, in particular the the *Leptospira* bacteria are *Leptospira interrogans* serogroup Australis serovar Bratislava.

The use of ethylenediaminetetraacetic acid to stabilise an immunogenic preparation of killed *Leptospira* bacteria in a liquid carrier, by dissolving the ethylenediaminetetraacetic acid in the carrier, is in particular embodied in a use wherein the preparation retains at least 25% of its antigenic mass (measured in ELISA units, when compared to the same preparation stored at a temperature of 2-8° C.) during a 3 month storage at a temperature above 18° C., in particular at 37° C.

EXAMPLES

The invention will now be further explained based on the following examples.

Example 1: Determining the efficacy of killed *leptospira* antigens as present in a commercially available vaccine in dogs Example 2: Determining the stability of *leptospira* antigens when stored at 37° C.

Example 3: Determining the stability of *leptospira* antigens formulated in EDTA when stored at 37° C.

Example 1

In this first example the efficacy of killed leptospira antigens as present in a commercially available vaccine was determined in conventional dogs, the antigens being formulated according to the label of the vaccine (100%), or diluted four times (25%). Defined concentrations of chemically inactivated *Leptospira* bacteria of the same type and serovars as present in the commercially available vaccine Nobivac L4 (available from MSD Animal Health, Boxmeer, The Netherlands; see also the 21 May 2012 publication of the Summary of Opinion of the CVMP of the European Medicines Agency regarding Nobivac L4), viz. *Leptospira interrogans* serogroup Canicola serovar Portland-Vere (*Leptospira canicola;* 5300 ELISA Units/ml), *Leptosira interrogans* serogroup Australis serovar Bratislava (*Leptospira Bratislava;* 1000 ELISA Units/ml), *Leptosipra interrogans* serogroup Icterohaemorrhagiae serovar Copenhageni (*Leptospira icterohaemorrhagiae;* 540 ELISA Units/ml) and *Leptosipra kirschneri* serogroup *Grippotyphosa* serovar Dadas (*Leptospira grippothyphosa;* 1000 ELISA Units/ml) were formulated in 10 mM PBS buffer at pH 7.2 (the buffer contained per liter water 8.9 gr NaCl, 0.2 gr KCl, 1.44 gr $Na_2HPO_4$ and 0.2 gr $KH_2PO_4$). The final formulation was filled into 3 ml vials, capped with rubber stoppers and sealed with aluminium crimp caps. This vaccine was stored at 2-8° C. (stable for up to 39 months). Next to this vaccine, a diluted vaccine was made by diluting the antigen in the same PBS buffer to reach a final concentration that contains 25% of the amount of Elisa Units per ml. The vaccines were tested as follows.

Husbandry of the Test Animals

Six-week-old conventional beagle dogs without detectable agglutinating serum antibodies against each of the *leptospira* serogroups mentioned here above were provided by a commercial supplier. In each of the studies, treatment groups (n=8) consisted of pups of both sexes and pups derived from different litters in order to prevent gender and litter effects interfering with treatment effects. The selected dogs were free of clinical abnormalities or disease prior to inclusion in these studies. Husbandry was the same in each study Vaccination In all studies the dogs were vaccinated twice subcutaneously, at the ages of 6 and 10 weeks with 1 ml of the respective vaccine.

Challenge

Challenge strains used were *Leptospira interrogans* serogroup Canicola serovar Canicola strain Moulton, *Leptospira interrogans* serogroup Icterohaemorrhagiae serovar Copenhageni strain CF1 (both strains received from the National Leptospirosis Reference Centre, KIT Biomedical Research, Amsterdam, The Netherlands), *Leptospira kirschneri* serogroup *Grippotyphosa* serovar Bananal/Liangguang strain 11808, and *Leptospira interrogans* serogroup Australis serovar Bratislava strain As-05-101 (both received from the United States Department of Agriculture, National Animal Diseases Center). For each of the four strains the following procedure was followed. The actual challenge material was prepared from a culture stored in liquid nitrogen, and passaged twice in Ellinghausen-McCullough medium modified by Johnson and Harris (Faine 1994; Clinical leptospirosis in humans, and clinical leptospirosis in animals; in *Leptospira* and Leptospirosis, CRC Press, 1994; pp 1-13, 199-225). The cultures stored in liquid nitrogen were re-isolates from experimentally infected animals: strains CF1 and 11808 were hamster kidney re-isolates, strain Moulton was a dog kidney re-isolate, and strain As-05-101 was a dog urine re-isolate. In all studies challenge was performed three weeks after the second vaccination using a combination of two challenge routes: intraperitoneal (IP) injection (2 ml) and conjunctival instillation (0.25 ml into the ventral conjunctival sac of each eye). Bacterial cell concentrations (cells/ml) in the challenge materials were determined by total direct microscopic count under dark-field microscopy and were between 0.5 and $10\times10^9$ cells/ml.

Examination

The dogs were examined regularly throughout each experiment, including measurement of body temperature after challenge using subcutaneous transponders. Blood and serum samples were taken by jugular venepuncture at regular intervals during the experiment for thrombocyte count, bacterial culture, PCR and leptospiral antibody assay. The serum samples were analysed by the microscopic agglutination test (MAT) against serogroups Canicola, Ictero, Grippo and Australis (Faine 1994). The microscopic agglutination titres were expressed as the reciprocals of the highest serum dilutions that induced 50% agglutination. Blood samples using EDTA as anticoagulant were used for assessment of thrombocyte counts after challenge using a Cell-Dyn 3500 cell counter (Abbott Laboratories, Abbott Park, Ill., USA).

EDTA or heparinised blood was used for re-isolation of challenge organisms from blood until day 21 post-challenge. For the same purpose urine samples were collected at regular intervals by cystocentesis, and kidney tissue taken at necropsy 4 weeks post-challenge was sampled and processed as described previously (Klaasen H L B M, Molkenboer M J C H, Vrijenhoek M P et al. Duration of immunity in dogs vaccinated against leptospirosis with a bivalent inactivated vaccine. *Vet Microbiol* 2003; 95:121-132). Samples of blood, urine and kidney tissue homogenate were inoculated into EMJH medium and cultures were incubated and examined as described by Klaasen.

Serum samples from days 0, 3 and 7 post-challenge were examined for the presence of DNA from challenge organisms with a real-time PCR targeting the secY gene. This PCR is a validated assay and is suitable for detection of DNA from all pathogenic *Leptospira* species (Ahmed A, Engelberts M F M, Boer K R et al. Development and validation of a real-time PCR for detection of pathogenic *Leptospira* species in clinical materials. *PLoS ONE* 2009; 4(9):e7093). The PCR was performed by the WHO/FAO/OIE and National Leptospirosis Reference Centre, KIT Biomedical Research, Amsterdam, The Netherlands. The PCR results were scored as positive, suspect or negative.

Dogs with severe clinical signs after challenge were humanely euthanised. Post-mortem examination including histopathological examination with special attention given to the detection of interstitial nephritis [Klaasen 2003] was undertaken in these cases.

The definition of a dog positive for infection was a dog with at least two positive samples of blood (by culture) or serum (by PCR) or urine/kidney (by culture) on different days or a dog with challenge-induced nephritis or clinical or haematological evidence (thrombocytopenia) for leptospirosis. The definition of a dog positive for renal infection (carrier animal, persistent shedder) was a dog with at least one positive sample of urine/kidney from day 14 post-challenge onwards or challenge-induced nephritis (demonstrated by histopathological examination).

Results

Below are the results for the four vaccines (undiluted and diluted). It shows that the vaccines, even at 25% dilution, still aid in protecting the dogs against an infection and protect almost all of the challenged animals against renal infection.

TABLE 1

Challenge strain *Canicola*

| Vaccine | Dogs positive for infection | Dogs positive for renal infection |
| --- | --- | --- |
| 100% *canicola* | 2/8 | 0/8 |
| 25% *canicola* | 1/8 | 1/8 |
| control | 8/8 | 8/8 |

TABLE 2

Challenge strain *Icterohaemorrhagiae*

| Vaccine | Dogs positive for infection | Dogs positive for renal infection |
| --- | --- | --- |
| 100% *ictero* | 0/7 | 0/7 |
| 25% *ictero* | 3/7 | 0/7 |
| Control | 7/7 | 7/7 |

TABLE 3

Challenge strain *Grippotyphosa*

| Vaccine | Dogs positive for infection | Dogs positive for renal infection |
| --- | --- | --- |
| 100% *grippo* | 0/8 | 0/8 |
| 25% *grippo* | 0/8 | 0/8 |
| Control | 7/8 | 6/8 |

TABLE 4

Challenge strain *Bratislava*

| Vaccine | Dogs positive for infection | Dogs positive for renal infection |
| --- | --- | --- |
| 100% *bratislava* | 0/8 | 0/8 |
| 25% *bratislava* | 0/8 | 0/8 |
| control | 6/8 | 1/8 |

Example 2

The killed *leptospira* bacteria are stable at 2-8° C. for at least 39 months (label of commercially available vaccine Nobivac L4). In this experiment it was determined whether the four antigens, formulated as indicated under Example 1 (100% vaccines) keep a level of at least 25% of ELISA units when stored at 37° C. during three months. The results are indicated here-beneath. The resulting antigenic mass (mean value of three different batches) is calculated as a percentage of the resulting antigenic mass of the same vaccines stored at 2-8° C.

TABLE 5

Percentage AG mass after storage at 37° C., compared to storage at 2-8° C.

| Ictero | Bratislava | Grippo | Canicola |
| --- | --- | --- | --- |
| 98 | 0 | 66 | 80 |

It shows that the killed whole cell antigens of the serogroups Icterohaemorrhagiae, Canicola and *Grippotyphosa* are relatively stable at 37° C., but that the antigens of the serogroup Australis, serovar Bratislava are highly unstable and do not reach the at least 25% level, set as a desired criterion for effectiveness as a vaccine. Although at room temperature, typically 20-25° C. the remaining level of antigenic mass may be higher, it is clear that stability, in particular for the Bratislava antigens, but also for the Grippothyphosa and Canicola antigens may be improved.

Further tests to improve stability were conducted only with the Bratislava antigens, expecting that any significant improvement will also improve the stability of the other antigens.

Example 3

Defined concentrations (1000 U/ml) of the same Bratislava antigens as described in Example 1 were formulated with different amounts of EDTA (ethylenediaminetetra acetic acid), by dissolving di-sodium ethylenediaminetetraacetate, in 10 mM of the same PBS buffer as mentioned in Example 1 (pH 7.2), until final concentrations were reached as indicated in table 6 below. Final formulations were filled into 3 ml glass vials, capped with rubber stoppers and sealed with aluminium crimp caps.

TABLE 6

Formulations used for stability experiments of *Bratislava* antigens

| Formulation | Content next to 1000 U/ml of killed whole cell *Leptospira bratislava* |
| --- | --- |
| 1 | PBS |
| 2 | PBS, 5 mM EDTA |
| 3 | PBS, 20 mM EDTA |
| 4 | PBS, 50 mM EDTA |

Half of the vials were incubated at 2-8° C., while the other half were incubated at 37° C. After 3 and 9 months vials were analysed using an antigenic mass ELISA test for *Leptospira bratislava* antigens. The antigenic mass was determined against the antigenic mass of a reference standard. The results are indicated here-beneath in Table 7. The resulting antigenic mass (mean value of three different vials) is calculated as a percentage of the resulting antigenic mass of the same vaccines stored at 2-8° C.

TABLE 7

Percentage AG mass after storage at 37° C., compared to storage at 2-8° C.

| Formulation | 3 months storage | 9 months storage |
|---|---|---|
| 1 | 0 | 0 |
| 2 | 84 | Not determined |
| 3 | 98 | 85 |
| 4 | 93 | 57 |

It shows that the stability of killed bacterial antigens of the serogroup Australis, serovar Bratislava is significantly increased by the addition of EDTA to the formulation. The desired criterion of at least 25% of the antigenic mass during a three months storage at 37° (and even considerably longer), compared to the vaccine stored under standard conditions has been met by adding various concentrations of EDTA. It may reasonably be expected, given the high resemblance of antigens, that by using the same measure, the stability of other killed bacterial *leptospira* antigens will be improved as well.

Example 4

Defined concentrations of the same four *Leptospira* antigens as described in Example 1 were formulated with two different EDTA concentrations (20 and 50 mmol/l) at pH 7.2. As a control, the antigens were put in a PBS buffer. The formulations were filled into 3 ml glass vials, capped with rubber stoppers and sealed with aluminium crimp caps.

Half of the vials were incubated at 2-8° C., while the other half were incubated at 27° C. After 8 weeks and 9 months vials were analysed using an antigenic mass ELISA test for *Leptospira* antigens. The antigenic mass was determined against the antigenic mass of a reference standard. The results are indicated here-beneath in Tables 8, 9, 10 and 11 for the different types of antigens. The resulting antigenic mass (mean value of three different vials) is calculated as a percentage of the resulting antigenic mass of the same vaccines stored at 2-8° C.

TABLE 8

Percentage AG mass of *Bratislava* antigens after storage at 27° C., compared to storage at 2-8° C.

| EDTA concentration [mM] | 8 weeks storage | 9 months storage |
|---|---|---|
| 20 | 99 | 73 |
| 50 | 100 | 77 |
| 0 (control) | 75 | 0 |

TABLE 9

Percentage AG mass of *Grippotyphosa* antigens after storage at 27° C., compared to storage at 2-8° C.

| EDTA concentration [mM] | 8 weeks storage | 9 months storage |
|---|---|---|
| 20 | 95 | 80 |
| 50 | 97 | 88 |
| 0 (control) | 100 | 59 |

TABLE 10

Percentage AG mass of *Icterohaemorrhagiae* antigens after storage at 27° C., compared to storage at 2-8° C.

| EDTA concentration [mM] | 8 weeks storage | 9 months storage |
|---|---|---|
| 20 | 100 | 90 |
| 50 | 100 | 98 |
| 0 (control) | 91 | 98 |

TABLE 11

Percentage AG mass of *Canicola* antigens after storage at 27° C., compared to storage at 2-8° C.

| EDTA concentration [mM] | 8 weeks storage | 9 months storage |
|---|---|---|
| 20 | 89 | 74 |
| 50 | 100 | 93 |
| 0 (control) | 74 | 51 |

It shows that the stability of various types of killed bacterial *leptospira* antigens are significantly increased by the addition of various concentrations of EDTA to the formulation in line with the expectations based on the results with the Bratislava antigens. The desired criterion of at least 25% of the antigenic mass during a three months storage at 27° (and even considerably longer), compared to the vaccine stored under standard conditions has been met.

The invention claimed is:

1. A composition containing an immunogenic cell preparation of killed *Leptospira* bacteria chosen from *Leptospira interrogans* serogroup Canicola serovar Portland-Vere, *Leptospira interrogans* serogroup Icterohaemorrhagiae serovar Copenhageni and *Leptospira kirschneri* serogroup *Grippotyphosa* serovar Dadas in an ethylenediaminetetraacetic acid solution, wherein the composition retains at least 25% of its antigenic mass during a 3 month storage at a temperature between 18° C. and 37° C.

2. The composition of claim 1, wherein the solution comprises 5 to 50 mmols of ethylenediaminetetraacetic acid per liter.

3. The composition of claim 2, wherein the solution comprises 20 mmols of ethylenediaminetetraacetic acid per liter.

4. The composition of claim 3, wherein the solution contains dibasic sodium phosphate.

5. The composition of claim 2, wherein the solution contains dibasic sodium phosphate.

6. The composition of claim 1, wherein the solution contains dibasic sodium phosphate.

7. A vaccine to protect an animal against an infection with *leptospira* bacteria, wherein the vaccine comprises a composition of claim 6.

8. A vaccine to protect an animal against an infection with *leptospira* bacteria, wherein the vaccine comprises a composition of claim 5.

9. A vaccine to protect an animal against an infection with *leptospira* bacteria, wherein the vaccine comprises a composition of claim 4.

10. A vaccine to protect an animal against an infection with *leptospira* bacteria, wherein the vaccine comprises a composition of claim 1.

11. A method of stabilizing an immunogenic preparation of killed *Leptospira* bacteria of claim 1 in a liquid carrier, comprising dissolving ethylenediaminetetraacetic acid in the liquid carrier.

* * * * *